United States Patent [19]

Ometz et al.

[11] Patent Number: 4,605,851
[45] Date of Patent: Aug. 12, 1986

[54] PROCESS AND DEVICE FOR DETECTING FOREIGN BODIES IN A LIQUID

[75] Inventors: Pierre H. M. Ometz; Jacques A. L. Labrador, both of Gironde, France

[73] Assignee: Societe Nationale Industrielle Aerospatiale, Paris, France

[21] Appl. No.: 462,448

[22] Filed: Jan. 31, 1983

[30] Foreign Application Priority Data

Feb. 1, 1982 [FR] France ............................. 82 01542

[51] Int. Cl.$^4$ ............................................. G01N 9/04
[52] U.S. Cl. ................................. 250/223 B; 356/427
[58] Field of Search ............ 250/562, 565, 564, 222.2, 250/223 B; 356/240, 441, 442, 427; 358/105; 209/522

[56] References Cited

U.S. PATENT DOCUMENTS

| | | | |
|---|---|---|---|
| 3,859,518 | 1/1975 | Sander | 358/212 |
| 4,204,230 | 5/1980 | Sprague | 358/212 |
| 4,281,354 | 7/1981 | Conte | 358/105 |

Primary Examiner—David C. Nelms
Assistant Examiner—James Gatto
Attorney, Agent, or Firm—Armstrong, Nikaido, Marmelstein & Kubovcik

[57] ABSTRACT

The invention relates to a process and device for detecting foreign bodies in a liquid, wherein the image of the apparent surface of the liquid in rotation in the immobilized recipients is formed, by reflection, diffraction, refraction or attenuation of the light coming from a source, on a matrix of reception and read cells. In the matrix each cell is perfectly delimited and its position is identified by numerization. A series of images is produced, of which a certain number are taken as reference and memorized. Each image is digitized and those images following the last memorized image is compared therewith cell by cell by a subtractor.

The results of such a subtraction are compared with a threshold and results overstepping the threshold involve delivering a signal to a processor which controls a sort device arranged to eliminate undesirable units.

13 Claims, 1 Drawing Figure

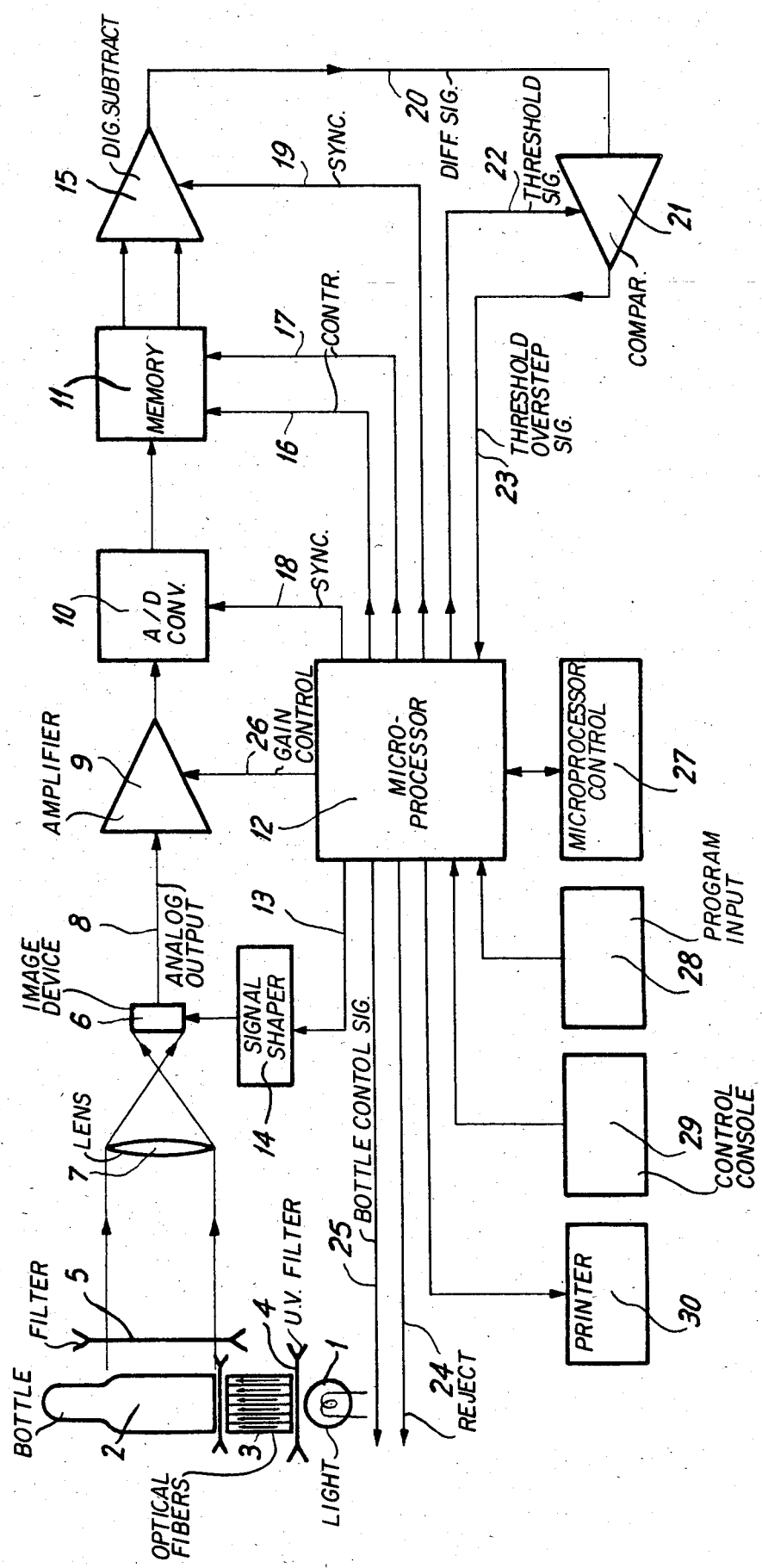

PROCESS AND DEVICE FOR DETECTING FOREIGN BODIES IN A LIQUID

The present invention relates to a process and a device for detecting foreign bodies, particularly solids, in a liquid and more especially to such process and device making possible automatic, rapid and reliable detection of the foreign bodies, such as solid particles or defects, present in a liquid contained in a recipient, transparent to the mode of detection, and undesirable above a predetermined apparent size, whatever their shape and nature.

The invention therefore generally relates to a process and device for non-destructive control, which may be carried out even after definitive closure of the recipient with a view to marketing it, and, in the following specification, the invention will be set forth with reference to the non-destructive control of pharmaceutical products such as ampoules and/or bottles of injectable products, without, however, being limited to this application which is given only by way of particular example.

In fact, it is known that injectable liquids presented in ampoules and/or bottles must be subjected to strict controls, with the particular object of detecting, after the ampoules or bottles have been sealed, the presence of defects of very varied nature, form and dimensions:- textile filaments (coming from clothing, filters, the atmosphere), granular particles, particles of glass or resulting from crystallization, dust, etc. . . . The purpose of this detection is to allow recipients containing inadmissible defects to be eliminated.

To this end, it has already been proposed to control ampoules of injectable products by carrying out a process consisting in placing an ampoule in movement, for example in driving it in rotation on itself about its longitudinal axis, then in immobilizing it suddenly in order to develop in the immobilized ampoule a substantially circular movement of the contents thereof.

The useful surface of the ampoule defined by its width (corresponding to its diameter, in the majority of cases) and the height of the liquid that it contains, is then scanned by a conventional television camera of analog type, and successive images thus obtained are compared, this enabling the presence of the particles contained in the liquid to be detected, reducing the risks of errors connected with the possible immobile and constant sources of parasitic signal, such as for example a defect in the material of which the ampoule is made, and/or a mark made on the ampoule.

However, the micro-instabilities in read-out of the images, inherent to analog scanning, are the cause of mediocre functioning, as the position of the zone scanned at each instant is determined by two variable electrical voltages, one defining the horizontal position (x-axis) and the other the vertical position (y-axis). As these voltages are continually variable and as each point of the image is not physically or mechanically defined, this results in a slight apparent difference in position of the image of the same point, from one read-out to the next, and therefore a fixed object, such as a letter or part of letter printed on the ampoule, is considered as mobile and consequently assimilated to a foreign body, when two successive images are compared with each other.

Such a detecting device therefore creates artificial defects per se and leads to numerous errors in detection, which renders use thereof incompatible with the reliability required in particular in the pharmaceutical domain. Moreover to proceed to comparisons according to an analog process involves instabilities which might be the cause of false rejections.

French Pat. Nos. 2,390,709 and 2,451,043 disclose detecting the presense of foreign matter in liquids by means of processes and apparatus enabling a zone of small area of the ampoule to be scanned. The ampoule, which is immobilized and whose contents are taken along in a pseudo-circular movement, as explained hereinabove, is interposed between a source of light, for which the ampoule is transparent, and a photodetector device, the axis of the source of light being common or at least very close to and substantially parallel to the optical axis of the photodetector device. The variation in light, resulting from passage in front of this zone of small area, of a foreign particle suspended in the liquid, and driven in rotation therewith in its pseudo-circular movement, enables it to be detected. This process of detection by occultation, since foreign bodies and deflects occult the incident light and create a reduction of the transmitted light received by the photodetector device, is also a process of continuous detection, since, during the control time, the photodetector device does not cease monitoring the ampoule.

In French Patent Application No. 2,451,043, the photosensitive surface of the photodetector device is constituted by a plurality of small light receivers, aligned along a strip parallel to a generatrix of the ampoule.

Ih the other French Patent Application mentioned hereinabove, No. 2,390,709, the photosensitive surface of the photodetector device is divided into a multiplicity of microphotoreceiving regions, which are disposed in one or more columns parallel to the axis of the ampoule, with or without overlapping in the direction perpendicular to the axis of the ampoule in the latter case and, possibly in addition, in one or more lines parallel to the direction perpendicular to the axis of the ampoule, at the level of the projection of the bottom of the latter. On the photosensitive surface, composed of twenty to one hundred and twenty distinct elements, each measuring from 0.01 to 1 mm$^2$, the relative surface area of the microphotoreceiver is rendered variable as a function of the limits of detection. The field of control may be modified as a function of the size of the transparent recipient, by modifying the number of microphotoreceivers used by means of a selection circuit. A switch enables a more or less high number of microphotoreceivers, disposed in one or more vertical rows, to be used, whose vertical dimensions are a function of the dimensions of the largest ampoule to be controlled, and possibly also disposed in one or more horizontal rows whose dimensions are a function of the largest width of the ampoules to be controlled, such horizontal row or rows being disposed so as to correspond to the base of the ampoules.

In these various embodiments, each photoreceiver element is constituted by a bundle of optical fibres terminating against a photoelectric converter element, such as a photo-diode, a photo-transistor or any other appropriate photoelectric cell, connected to at least one amplifier which is specific thereto, in an analog circuit for particle detection, comprising a capacitor, eliminating the continuous component of the signal, and a threshold comparator of which the threshold corresponds to a standard reference value previously fixed and set for the level of detection of the foreign particles. An OR circuit then gathers together the signals coming from the different threshold comparators, and controls elimination of the ampoule if one of the latter delivers a threshold overstep signal.

At best, the surface monitored by these known devices corresponds to a zone of control in the form of an upturned T, of which one bar, parallel to the axis of the ampoule, coresponds to a generatrix or to a thin strip on the ampoule, of width much less than that of the ampoule, and of which the other bar, perpendicular to the axis of the ampoule, corresponds to a thin horizontal strip against the base of the ampoule, of which it covers the diameter, and of height much less than that of the liquid in the ampoule.

These devices do not enable the reliability required in the control of pharmaceutical products to be attained, as the monitoring is limited to a very small proportion of the apparent surface of the liquid, and generally to a more or less wide generatrix remaining fixed but always much less than the width of the ampoule, making it difficult to control marked or printed ampoules. In fact, it often happens that the mark printed on the ampoule occults an important fraction of the small zone monitored, and that a particle in suspension cannot be detected. Moreover, the quantity of light deflected to the receiver or occulted depends on the position and the orientation of each particle in the recipient. Thus the probability of detection of the particle through a narrow generatrix decreases substantially.

U.S. Pat. Nos. 3,777,169 and 3,598,907 disclose employing a process of detection consisting in comparing two successive images of an ampoule illuminated on a black background (the image being produced only by the light diffracted, reflected or deflected from the impurities in a direction substantially perpendicular to the illumination) produced analogically by means of a scanning camera. Only the light dots producing an analog voltage higher than a certain threshold are taken into account. Said voltage is then shaped in a square or rectangular signal (false digitalization which is independant of the value by which the threshold is overstepped. A substraction of two successive images, if it is not zero, signifies the presence of an impurity. One of the major drawbacks of this technique, in addition to those inherent in the technique of scanning, resides in the presence of a threshold which "filters" the reception before the processing of the signal proper. The role if this threshold is to eliminate noise but, as shown in U.S. Pat. No. 3,777,169, the useful signals are often of the same order of magnitude as the noise itself. It is then recommended to vary this threshold between the first and the second image, in order to avoid noise and parasitic variations.

It is an object of the present invention to overcome the drawbacks presented by the known control devices and processes, and to allow detection which is disturbed neither by a mark printed on the recipient nor by a defect in the recipient itself, so that the recipients containing at least one undesirable particle in a liquid contained therein can be sorted automatically, rapidly and reliably.

To this end, the invention first relates to a process whereby a liquid contained in a recipient transparent to a certain light is placed in movement, and is illuminated so that an image produced by reflection, diffraction or attenuation, corresponding substantially to all the continuous apparent surface of the liquid contained in said recipient, is formed on a sensitive surface.

According to one of the principal features of the invention, at an initial instant, a first image of this apparent surface as formed on said sensitive surface is analyzed point by point, and the results of this analysis are digitized and memorized; at a subsequent instant, a second image is analyzed point by point, the results of the second analysis are substracted point by point from the memorized results of the first analysis and each of the differences is compared with at least one pre-established threshold indicative of foreign bodies considered as inadmissible. A series of successive images made at previously selected intervals of time, which may for example be of the order of 20 ms, may advantageously be memorized then compared with one another in two's.

Due to the process according to the invention, the defects connected with the manufacture of the recipient and/or the existence of a mark thereon are not retained, when comparing two successive images, as they produce the same light signal, at the same precisely located spots on each of the two images.

A particle circulating in the liquid contained in the recipient analyzed is therefore detected reliably, such detection being based on the differences in light signals created by the particle circulating in this liquid, which differences may in addition be known quantitatively.

It should be noted that the light signal threshold may be selected during a previous standardization operation, cpnsisting in examining recipients containing defects serving as standards according to the reference system for controlling a liquid contained in a recipient transparent to the mode of detection, forming the subject matter of Applicants' French Patent Application No. 80-14621.

According to another feature of the invention, the value of the electrical signal provoked by the passage of the image of the same defect on the sensitive surface being a function of its time of passage, which increases when the rotation of the liquid slows down, the value or the or each threshold significant of comparison varies as a function of time, to take into account the slowing down of the movement of the liquid in the recipient, and to obtain a substantially constant threshold of detection of the inadmissible foreign bodies.

The variation of the or each threshold significant of comparison is preferably controlled at predetermined intervals of time and is effected according to increasing values of such threshold or thresholds.

It is well known that the rotation of the liquid contained in the recipient may bring about a phenomenon of vortex or an instability of the surface of separation between the liquid and the air. These phenomena cause variable light signals which must not be interpreted as defects. To this end, and according to a further feature of the invention, the comparisons in two's of the successive images are effected on zones increasing from the image of the bottom of the recipient towards the image of the surface of the liquid, so as not to include the afore-mentioned vortex or instability. This measure enables control of the recipient to be started very soon after the sealing thereof. According to a further feature of the invention, a plurality of adjacent recipients are controlled simultaneously and the location, on the sensitive surface, of at least one zone in which the result of the substraction in two's is greater than said pre-established threshold, controls the emission of at least one signal for identifying the recipient in question for elimination thereof.

The invention also relates to a device for carrying out the process which has been described, which comprises a source of light, for which the recipients are transparent, as well as a photosensitive surface, in which the axis of the source of light is substantially perpendicular to the optical axis of the photosensitive surface, and its optics. According to the invention, this device comprises:

a sensitive surface consituted by a plurality of micro-photoreceiving regions in the form of a matrix of adjacent receiving and read cells, defined mechanically and electrically, excitable and readable independently of one another, the surface of the matrix being greater than the image of the apparent surface of the liquid contained in the or each recipient, said matrix of photosensitive cells constituting an element of an integrated opto-electronic circuit which also comprises auxiliary control and transfer circuits and a serial output of analog type, of which the signal, after exterior amplification, is applied to the input of an analog-digital converter, of which the output may be stored in a memory whose minimum capacity corresponds to an image, a first comparison member showing, by subtraction, the difference between two images of which at least the first is memorized, and taken as reference, and a second comparison member comprising said differences with at least one threshold significant of comparison, and delivering a signal when at least one of the said differences is greater than said significant threshold.

Still according to the invention, the integrated circuit comprising the matrix of the photodetectors and its auxiliary transfer and control circuits may comprise other devices such as for example an analog-digital converter; in this case, the output is composed of a plurality of channels, one per bit of resolution of the converter and one per control or synchronization channel.

The first comparison member is preferably a subtractor of which the output is connected to the input of the second comparison member, in the form of a threshold comparator, delivering a threshold overstepping signal to a general control member and receiving at least one digital threshold value from the latter, which simultaneously ensures synchronization of the subtractor, the analog-digital converter and the threshold detector, and delivers on the one hand to the memory, signals controlling memorization and signals controlling read-out of the memory, and on the other hand to the mechanism for sorting the recipients, a switching order for each recipient controlled.

Moreover, the general control member also ensures synchronization of a member for controlling and shaping the signals useful for the matrix of photosensitive cells.

Moreover, a variable gain analog amplifier is interposed between the output of the matrix of photosensitive cells and the input of the analog-digital converter, the variation of the gain being obtained by digital control, at predetermined intervals, from the general control member, so that the gain decreases from the immobilization of the or each recipient to be controlled. This variation of the gain may be controlled at intervals of time chosen experimentally and the variable gain analog amplifier makes it possible to respect the detection threshold fixed by the prior adjustment of the device with recipients containing standard defects, as mentioned hereinbefore.

In a preferred embodiment, the general control member of the device is a microprocessor also connected to a second memory, containing the general programs ensuring the train of the sequences of operation and making it possible to obtain the series of successive images, the memorizations and comparisons of the images taken in two's; to an input member of the particular programs, enabling in particular digital values of the comparison thresholds and digital control of the variable gain to be obtained; to a control console; to a printer recording the conditions of control and the results; and finally to the mechanism for gripping and handling the recipients, to which the microprocessor delivers a mechanical order sequencing signal. The microprocessor may also control one or more other microprocessors to which it delegates certain tasks, such as for example the control of the subtractor member, the comparison with the threshold(s), the synchronization of the analog-digital converter.

In a preferred embodiment, the matrix of photosensitive cells of the device according to the invention is constituted by the sensitive surface of a charge-transfer television camera, comprising for example 144 lines of 208 elementary photosensitive cells integrated on a silicon chip, which also comprises control, transfer and output circuits.

The controlled recipients may be illuminated axially or laterally and the matrix of photosensitive cells, whose optical axis is substantially perpendicular to the axis of the or each recipient, receives the image of the apparent surface of the liquid formed by a lens receiving the light reflected, diffracted, refracted or attenuated by the contents and the walls of the or each recipient.

If need be, in order not to deteriorate the quality of the pharmaceutical product contained in the recipients, an ultraviolet filter may be disposed between the source of light and the recipient.

If need be, an anti-dazzle filter, eliminating the wave lengths which may be detrimental to the quality of detection, taking into account the nature of the material used for the markings of the recipients, may be disposed before or after the recipients. Similarly, a filter placed between the recipient to be controlled and the source limits undesirable overheating by eliminating the useless infrared wave lengths.

Furthermore, a bundle of optical fibres may be used for conducting the light from the source up to the vicinity of the or each recipient.

By using the device according to the invention, a plurality of recipients are preferably controlled simultaneously. If one of such recipients contains a foreign body considered as being inadmissible, a signal is emitted further to the comparison of two successive images memorized, and this signal, comprising the identification of the recipient to be rejected by localization on the sensitive surface of the camera, is processed by the microprocessor which controls elimination of the recipient which has been judged defective.

The process and device according to the invention therefore use a method of detection by reflection and diffraction, so that the foreign bodies in the liquid produce an increase in light received by the photosensitive surface. To make the latter, a sensitive camera surface is used, constituted by an integrated circuit comprising a large number of elementary cells (for example 30,000), which are, however, each well defined geometrically, and the output signals from these cells all pass via the same channel, which amplifies, digitalizes and memorizes the signals received.

It is to be noted that each elementary cell, being mechanically delimited definitely and stably, is well identified and the light received is digitalized (for example between 0 and 255). This digitalization which is systematic, permits the device to proceed with memorizing without error or instability and the subsequent comparisons are more accurate. The digitalized images are then compared in two's so that the monitoring is quasi continuous but nevertheless made in a digital manner. The principle of detection is that it suffices that the difference between the same point of two successive images be greater than a certain threshold value, which may be variable as a function of the time, to control elimination of the controlled recipient. It is therefore a difference between two signals delivered from the same point which is demonstrated, which is very different as the signal received by each point of each image either oversteps a fixed threshold, or does not, in absolute manner. Moreover, the very large number of cells of the photosensitive surfaces enables several recipients to be controlled simultaneously, whilst taking into account almost the whole of the apparent surface of the liquid contained by each. Finally, the method of detection by reflection and diffraction simultaneously procures the advantage that it is also possible to control the level of filling of the recipients, by detecting the position of the surface of separation between the liquid and the air, which constitues a zone of extreme brilliance over the whole width of the liquid contained in the recipient.

The invention will be more readily understood on reading the following description with reference to the accompanying drawings, in which:

The single FIGURE symbolically shows the device used for carrying out the process according to the invention.

The device shown symbolically in the single FIGURE comprises a source of light 1, illuminating axially and from underneath a group of five adjacent bottles 2 to be controlled, made of a material transparent to the light of source 1, and containing an injectable pharmaceutical product in which there are possibly some particles in suspension.

The source of light 1 may comprise a low-voltage quartz/halogen lamp, a reflector and, if need be, an optical system for concentration. A bundle of optical fibers 3 conducts the incident light from the source 1 up to the immediate vicinity of the bottom of the bottles 2, and if necessary a filter 4 against UV Rays is disposed between the source 1 and these bottles 2 in order not to deteriorate the injectable product, if necessary. An optical system for rendering pseudo cylindrical the beam of light inside the bottle and a diaphragm (neither being shown) reducing the luminous section in the inner diameter of the bottles 2 may also be provided between the bundle of optical fibers 3 and these bottles 2 in order to diminish the lighting of printings and defects in the bottles 2.

The light reflected and diffracted by the bottles 2 and their contents (liquid and particles in suspension) is filtered by an anti-dazzle filter 5, eliminating the wave lengths which may be detrimental to the quality of detection, taking into account the nature of the material or materials used for making the markings or inscriptions on the bottles 2, and the image of these bottles 2 is formed on a photosensitive surface 6 by a lens 7, suitably chosen taking into account the desired magnification, the distance between the bottles 2 and the photosensitive surface 6, and the luminosity, in accordance with the rules of the art.

The surface 6 is constituted by the sensitive surface of a charge-transfer television camera, made in the form of an integrated opto-electronic circuit. This sensitive surface is in the form of a matrix of adjacent elementary reception and read cells which are physically and mechanically defined and fixed with respect to one another, and capable of being excited independently of one another. This matrix is constituted by 144 lines of 208 elementary photosensitive cells, or a total of 29,952 cells, of which each is in rectangular form and measures 30 microns in length and 28 microns in width, which represents a surface area of $84 \times 10^{-5}$ mm$^2$.

This photosensitive surface 6, which may count 30,000 cells, or more, therefore receives the image of all, or virtually the whole of the apparent surface of the liquid contained in each of the five bottles 2, this apparent surface being defined by the width of a bottle 2 and the height of the liquid which it contains. About 3000 cells of the surface 6 are thus used for receiving the image of one bottle and for controlling the apparent surface of the liquid that it contains.

These cells allow the scanning, point by point, of this apparent surface of the liquid, whilst the content of the bottle is set into motion in the immobile bottle, due to the vortical motion given to the liquid by previously rotating then suddenly stopping the bottle 2, by means of a mechanical device for gripping and maneuvering the bottles (not shown), ensuring transfer, rotation and, at the end of control, sorting thereof.

The integrated circuit comprising the photosensitive surface 6 and its interior auxiliary circuits, is connected by a single serial analog output 8 to the input of a variable gain analog amplifier 9, whose role will be explained hereinbelow, and itself connected by its output to the input of analog-digital converter 10. The latter supplies a memory 11 whose minimum capacity is, in this example, two images of a group of five bottles 2.

At an initial time $T_o$, determined by a microprocessor 12 constituting a general control member of the device, and transmitted by a synchronization line 13 to a member 14 for controlling and shaping the signals useful for the integrated circuit of surface 6, the assembly of the cells of this latter point by point analysis, the image of the apparent surface of bottles 2, and the light signal received by each elementary cell is memorized at 11, after amplification at 9 and numeration at 10 (its numeration will for example be a number included between 0 and 255 depending on the nature of the signal). In this way, a first reference image is constituted.

At a subsequent instant $T_1$, the same surface is again analyzed and the light signal received by each elementary cell is again memorized at 11, in the same way, to constitute a second image.

The two images obtained at instants $T_o$ and $T_1$ are then compared point by point by a subtractor 15, connected to the output of the memory 11, which receives from the microprocessor 12 its respective input and output control orders via control lines 16 and 17, whilst the analog-digital converter 10 and the subtractor 15 are respectively controlled from the microprocessor 12 via synchronization lines 18 and 19.

Similarly, fresh images are memorized in pairs, at instants $T_n$ and $T_{n+1}$, at previously chosen intervals of time which may for example be of the order of 20 ms, then again compared. According to the invention, images of instants $T_{n+1}$, $T_{n+2}$ ... may be compared with the image of $T_n$ which is taken as a reference. It is not necessary to memorize images which are not used as a reference. From the output of the analog/digitial converter, said images may be compared directly with the memorized reference. The signals corresponding to the possible differences, bearing witness to the presence of particles in the liquid, are transmitted via line 20 from the output of subtractor 15 to the input of a threshold comparator 21.

It is clear that defects in the bottles made at manufacture or defects due to the presence of a marking on the bottles, which are fixed defects, produce the same light signal at the same spots precisely located on each image. A comparison of these two images therefore reveals no difference, and these defects are not retained.

On other hand, a particle circulating the liquid contained in one of the controlled bottles is reliably detected, due to the differences in light signals created by this particle and presented by each successive image.

In order that only foreign bodies or solid particles considered as being inadmissible as their size is greater than a certain limit, be detected, a threshold significant of comparison, corresponding to a threshold significant of pinpoint light signal difference, is chosen in the course of a previous standardization operation, consisting in the examination of bottles identical to those to be controlled, and containing standard defects, according to Applicants' French Patent Application No. 80 14621 relating to a "reference system for controlling a liquid contained in a recipient transparent to the mode of detection".

The numerical value of the chosen threshold significant of comparison is transmitted from the microprocessor 12 to the threshold comparator 21 via line 22, and a threshold overstep signal is delivered at the output of the comparator 21 and transmitted to the microprocessor 12 via line 23, if a difference signal at its input is greater than the threshold.

The device therefore ensures comparison of the differences between the signals of two successive images with the threshold chosen.

Simultaneously, the processing of the signals received by the microprocessor 12 allows that or those of the zones of the photosensitive surface 6, each appropriated to the control of the image of the apparent surface of the liquid contained in a bottle, for which a difference at least between the pinpoint light signals memorized during the taking of the two successive images has proved greater than the threshold, to be located on said photosensitive surface 6.

Further to such location, the microprocessor 12 communicates, via a line 24, a switching order for each controlled bottle to a mechanical device for sorting the bottles on leaving the control device.

In synchronism, the microprocessor 12 also controls the mechanical device for gripping and handling the bottles 2, which the control device comprises, to ensure motion of the bottles 2 on themselves and to develop the vortical motion of their contents, then the sudden immobilization thereof, and the corresponding orders are transmitted via a line 25 for sequencing the mechanical operations.

As the rotation of the contents of the bottles 2 therein may bring about a phenomenon of vortex or an instability of the surface of separation between the liquid and the air in each bottle 2, the photosensitive surface 6 may receive variable light signals which must not be interpreted as witnessing the presence of inadmissible particles in the liquid. To this end, the microprocessor 12 controls the member 14 for controlling and shaping the signals useful for the photosensitive surface 6, so that increasingly larger zones of the photosensitive surface 6 increasing from that part of the latter receiving the image of the bottom of the bottles 2 towards the part receiving the image of the surface of the liquid in the bottles 2, are activated to allow pairs of successive images to be taken and then successively compared, without including the image of the vortex or of the instability. This measure therefore enables the bottles 2 to be controlled very soon after they have been immobilized.

Moreover, as the rotation of the contents of the bottle 2 therein progressively slows down, the time of passage of the image of the same foreign body on an elementary cell of the matrix of the sensitive suface 6 increases. Now, the value of the electrical signal delivered by this elementary cell is, within certain limits, a function of this time of passage, therefore also the difference in two electrical signals delivered at successive instants. The detection device makes it possible to vary the value retained as significant difference between the electrical signals coming from each elementary cell, i.e. the threshold significant of comparison, as a function of time, in order to maintain constant the previously chosen level of detection.

This is obtained due to the microprocessor 12, communicating via line 22 a numerical value increasing in time from the threshold significant of comparison to the threshold comparator 21. However to complete the action of this variation of the threshold significant of comparison, the microprocessor 12 controls via line 26 the variable gain analog amplifier 9. The value of the gain of this amplifier 9 is chosen by digital control, and its variation is controlled at intervals of time chosen experimentally, so that the gain takes values decreasing in time from the mechanical immobilization of the bottles 2, following rotation thereof, and the amplifier 9 thus controlled makes it possible to respect the level of detection fixed by the prior adjustment of the detection device by means of bottles containing standard defects.

When a vortex motion in the bottles 2 is much attenuated, and therefore when the activated zone of the photosensitive surface 6 corresponds to the whole surface thereof, so as to control the whole image of the apparent surface of the liquid contained in the botles 2, the detection device also makes it possible to control the level of filling of the bottles 2, by detecting the position of the surface of separation between the liquid and the air in each bottle 2, this surface of separation constituting a zone of considerable brilliance over the whole width of the liquid contained in the bottle 2.

The general programs ensuring the train of the sequences and making it possible in particular to obtain the start of the mechanical movements of the recipients, the successive images, the memorizations and comparisons of images, are stored in a memory 27 connected to the microprocessor 12 to which is also connected a member 28 for entry of the particular programs such as a magnetic reader and recorder, allowing introduction of the values of the threshold significant of comparison of the comparator 21, the values of the gain of the amplifier 9, instructions relative to the selection of the increasing zones of the photosensitive surface 6, as a function of time, and to the selection of the maximum zone of the surface 6 activated as a function of the size and number of the bottles 2 to be controlled, etc.

Furthermore, it will be noted that the photosensitive surface may comprise a plurality of occulted cells of which the output signal, interpreted by the assembly processing logic, constitutes a black background reference allowing an overall correction of the device as a function of the deflections due in particular to temperature.

Finally, a control console 29 and a printer 30, recording the conditions and results of the controls, are connected to microprocessor 12.

The invention is not limited to the embodiment which has just been described. In a variant, to take into account the slowing down of rotation of the liquid in the bottles 2, the interval of time separating two memorized and compared images may be increased correlatively, so that the image of the or each undesirable particle has covered a distance greater than the dimensions of an elementary photoelectric cell.

We claim:

1. The process for detecting foreign bodies, particularly solids, in a liquid contained in at least one recipient transparent to a certain light, whereby the liquid is placed in movement and is illuminated so that an image thereof produced by reflection, diffraction or attenuation, corresponding substantially to all the continuous apparent surface of the liquid contained in said recipient, is formed on a light sensitive surface,
   wherein, at an initial instant, a first image of said apparent surface as formed on said light sensitive surface is analyzed point by point, and the analog values of the results of this analysis are digitalized and memorized;
   at a subsequent instant, a second image is analyzed point by point, the analog values of the results of the second analysis are digitalized and compared by digital subtraction point by point from the memorized results of the first analysis, and
   the numerical value of each of said digital differences is compared with at least one pre-established digital numerical threshold indicative of foreign bodies considered as inadmissible,
   wherein the value of said threshold significant of comparison varies as a function of time to take into account the slowing down of the movement of said liquid in the recipient and to obtain a substantially constant threshold of detection of the inadmissable foreign bodies, and wherein the difference of illumination taken into account on two different images, of which at least one is memorized, is compared with said varied threshold of detection.

2. The process of claim 1, wherein a series of successive images is made at previously selected intervals of time, digitalized and memorized, and then each of said images is successively compared with at least one of said memorized digitalized images taken as a reference.

3. The process of claim 1, wherein the variation of the threshold significant of comparison is controlled at pre-determined intervals of time, according to the increasing values of such threshold.

4. The process of claim 1, wherein the comparisons in two's of the successive images are effected in increasingly larger zones of said light sensitive surface, increasing from the image of the bottom of the recipient towards the image of the surface of the liquid.

5. The process of claim 1 wherein a plurality of adjacent recipients are controlled simultaneously and the location, on the sensitive surface, of at least one zone in which the result of the subtraction in two's of the successive images is greater than said pre-established threshold, controls the emission of at least one signal for identifying the recipient in question for elimination thereof.

6. A device for detecting foreign objects, particularly solids, in a liquid, comprising a source of light for illuminating at least one recipient containing said liquid and a detector assembly including an optical system and a photosensitive surface in which the direction of the light illuminating the recipient is substantially perpendicular to the optical axis of the detector assembly, wherein said device comprises:
   a light sensitive surface comprising a plurality of microphotoreceivers in the form of a matrix of adjacent receiving and read cells, defined mechanically and electrically, excitable and readable independently of one another, the surface of said matrix being greater than the image of the apparent surface of the liquid contained in the recipient, defined by the width of the recipient and the height of the liquid therein, said matrix of photosensitve cells being connected to an integrated opto-electronic circuit, of which the output is connected by a serial analog channel to the input of an analog-digital converter, of which the output is connected to the input of a memory whose minimum capacity corresponds to the digitalized representation of an image,
   a first comparison member providing, by subtraction, the differences between two images of which at least the first has been memorized, for constituting a reference,
   and a second comparison member comparing said differences with at least one pre-established significant threshold and delivering a signal when at least one of said differences is greater than said significant threshold.

7. The device of claim 6, wherein the first comparison member is a subtractor of which the output is connected to the input of the second comparison member, in the form of a digital threshold comparator, delivering a threshold overstepping signal to a general control member and receiving at least one digital threshold value from the latter, which simultaneously ensures synchronization of the subtractor and the analog-digital converter, and delivers on the one hand to the memory, signals controlling memorization and signals controlling read-out of the memory, and on the other hand to a mechanism for sorting the recipients, a switching order for each recipient controlled.

8. The device of claim 7, wherein the general control member further ensures synchronization of a member for controlling and shaping the signals useful for the matrix of photosensitive cells.

9. The device of claim 6, wherein a variable gain analog amplifier is interposed between the output of the matrix of photosensitive cells and the input of the analog-digital converter, the variation of gain being obtained by digital control, at predetermined intervals, from the general control member, so that the gain decreases from the immobilization of the recipient to be controlled.

10. The device of claim 7, wherein the general control member is a microprocessor, also having connected thereto:
   a microprocessor control including a second memory, containing the general programs ensuring the train of the sequences of operation and making it possible to obtain the series of successive images, the memorizations and successive comparisons of the images taken in two's, an input member of particular programs, enabling in particular digital values of the comparison thresholds and digital control of the variable gain to be obtained, a control console, a printer for recording the conditions of control and the results, and a mechanism for gripping and handling the recipients, to which the microprocessor delivers a mechanical order sequencing signal.

11. The device of claim 7, wherein the matrix of photosensitive cells is constituted by the sensitive surface of a charge-transfer television camera, said surface constituting an element of the integrated opto-electronic circuit, which also comprises control, transfer and output circuits.

12. The device of claim 7, further comprising an antidazzle filter disposed between the recipient and the photosensitive surface eliminating the wave lengths detrimental to the quality of detection as a function of the material or materials used for making the markings on the recipient.

13. The device of claim 6, wherein the sensitive surface comprises a plurality of occulted receiving cells furnishing a black background reference signal to correct the deflections due to the variations in temperature.

* * * * *